(12) United States Patent
Riesinger

(10) Patent No.: US 10,603,219 B2
(45) Date of Patent: Mar. 31, 2020

(54) LIQUID-PERMEABLE PRIMARY DRESSING WITH A SILICONE COATING

(71) Applicant: BSN MEDICAL GMBH, Hamburg (DE)

(72) Inventor: Birgit Riesinger, Munster (DE)

(73) Assignee: BSN medical GmbH, Hamburg (DE)

( * ) Notice: Subject to any disclaimer, the term of this patent is extended or adjusted under 35 U.S.C. 154(b) by 503 days.

(21) Appl. No.: 14/794,189

(22) Filed: Jul. 8, 2015

(65) Prior Publication Data

US 2016/0000610 A1 Jan. 7, 2016

Related U.S. Application Data

(63) Continuation of application No. PCT/EP2014/050331, filed on Jan. 9, 2014.

(30) Foreign Application Priority Data

Jan. 9, 2013 (DE) .......... 10 2013 100 157

(51) Int. Cl.
A61F 13/00 (2006.01)
A61F 13/02 (2006.01)

(52) U.S. Cl.
CPC .. *A61F 13/00068* (2013.01); *A61F 13/00017* (2013.01); *A61F 13/00025* (2013.01); *A61F 13/00063* (2013.01); *A61F 13/0206* (2013.01); *A61F 13/0216* (2013.01); *A61F 2013/00217* (2013.01); *A61F 2013/00314* (2013.01)

(58) Field of Classification Search
CPC .......... A61F 13/00068; A61F 13/00017; A61F 13/00025; A61F 13/00063; A61F 13/0206; A61F 13/0216; A61F 2013/00217; A61F 2013/00314

See application file for complete search history.

(56) References Cited

U.S. PATENT DOCUMENTS

| | | | | |
|---|---|---|---|---|
| 3,885,559 | A * | 5/1975 | Economou | A61F 13/0203 602/55 |
| 5,340,363 | A | 8/1994 | Fabo | 604/304 |
| 8,377,015 | B2 * | 2/2013 | Ueda | A61F 13/0203 156/329 |
| 2002/0108564 | A1 * | 8/2002 | Gruenewald | B05C 5/027 118/125 |

(Continued)

FOREIGN PATENT DOCUMENTS

| | | |
|---|---|---|
| CN | 101969902 A | 2/2011 |
| JP | 200995476 | 5/2009 |

(Continued)

OTHER PUBLICATIONS

International Preliminary Report on Patentability issued in corresponding foreign application, PCT/EP2014/050331, pp. 1-8 (dated Jul. 23, 2015).

(Continued)

*Primary Examiner* — Adam Marcetich
*Assistant Examiner* — Jessica R Arble
(74) *Attorney, Agent, or Firm* — Rankin, Hill & Clark LLP

(57) ABSTRACT

The present invention relates to a fluid-permeable primary dressing in strip form, having pores, perforations or honeycomb lattices, which enable the passage of fluid, further having a coating of a material comprising silicone.

10 Claims, 8 Drawing Sheets

(56) References Cited

U.S. PATENT DOCUMENTS

| | | | |
|---|---|---|---|
| 2004/0126413 A1* | 7/2004 | Sigurjonsson | A61F 13/0203 424/445 |
| 2007/0135787 A1* | 6/2007 | Raidel | A61F 13/15707 604/383 |
| 2009/0093779 A1* | 4/2009 | Riesinger | A61F 13/00029 604/290 |
| 2011/0160686 A1 | 6/2011 | Ueda et al. | |
| 2012/0095380 A1 | 4/2012 | Gergely et al. | 602/45 |
| 2013/0172843 A1 | 7/2013 | Kurata | 604/372 |
| 2014/0171851 A1* | 6/2014 | Addison | C09J 7/22 602/55 |
| 2014/0350494 A1* | 11/2014 | Hartwell | A61F 13/0216 604/319 |

FOREIGN PATENT DOCUMENTS

| | | | |
|---|---|---|---|
| JP | 2009247380 | 10/2009 | |
| WO | WO 93/19710 | 10/1993 | |
| WO | WO 2007/118652 | 10/2007 | A61F 13/00 |
| WO | WO 2011/152368 | 12/2011 | |
| WO | WO 2012/104584 | 8/2012 | A61F 13/02 |
| WO | WO 2012/140441 | 5/2013 | |
| WO | WO 2013/121006 | 8/2013 | A61F 13/00 |

OTHER PUBLICATIONS

International Search Report issued in corresponding foreign application, PCT/EP2014/050331, pp. 1-2 (dated Jul. 17, 2014).

Written Opinion issued in corresponding foreign application, PCT/EP2014/050331, pp. 1-5 (dated Jul. 9, 2015).

JP Notice of Rejection, JP 2015-552048, pp. 1-5, (dated Oct. 24, 2017).

EP Examination Report, EP 14700195.2, pp. 1-6, (dated Dec. 12, 2017).

Office Action dated Sep. 4, 2018 for the corresponding Chinese Patent Application No. 201480009534.9; English translation.

* cited by examiner

LIQUID-PERMEABLE PRIMARY DRESSING WITH A SILICONE COATING

CROSS-REFERENCE TO RELATED APPLICATIONS

The present application is a continuation and claims priority under 35 U.S.C. § 120 and § 365(c) to PCT International Patent Application PCT/EP2014/050331, filed Jan. 9, 2014, which claims priority to German Patent Application No. 10 2013 100 157.2, filed Jan. 9, 2013, each of which are incorporated herein by reference in their entireties.

BACKGROUND

The present invention relates to a primary dressing according to the preamble of claim 1.

Primary dressings are known from the state of the art. They are applied onto the wounds to be treated as a wound contact layer, before the actual wound dressing is applied. They can have various types of properties, for example decreasing the adhesion, preventing growth into the wound dressing or contributing to balanced fluid management.

In other embodiments, primary dressings can be provided as an integral component of the covering of a wound dressing, wherein they perform similar or identical functions there as in the loose form.

In principle, primary dressings also enable prolongation of the wear time of the actual wound dressing on the wound, which decreases the frequency of dressing changes and thus reduces traumatic events. However, many types of wounds for which use of primary dressings is indicated (pressure ulcers, leg ulcers, burn wounds, etc.) are highly sensitive to adherence, and have a traumatic response to dressing changes, which is extremely painful for the patient and further serves to greatly impair the wound healing process.

SUMMARY OF THE INVENTION

The purpose of the present invention is thus to provide a primary dressing which enables a longer wear time on the wound.

A further problem addressed by the present invention is that of providing a primary dressing which enables an atraumatic change of dressing.

These problems are solved by the features of the independent patent claims. The subclaims describe preferred embodiments.

According to this, a fluid-permeable primary dressing is provided in strip form, having pores, perforations or honeycomb lattice which enable passage of liquid, further having a coating of a material comprising silicone.

Such primary dressings are applied onto the wounds to be treated as a wound contact layer, before the actual wound dressing is applied. They can have various types of properties, for example decreasing adhesion or contributing to balanced fluid management.

The term "material comprising silicone", as used here, relates to both silicone-coated material and material consisting of all silicone.

The silicone can be designed such that it has a decidedly adhesive action such that the primary dressing adheres to the wound, but also such that it prevents adhesion of the sometimes often to be changed secondary dressing to the wound, or indeed granulation into the same.

The adhesive properties of silicones can technically be very precisely adjusted to ensure (a) secure adhesion, without removal of the primary dressing causing pain, for example due to adhering body hair, or even having a traumatic effect or (b) that the primary dressing does not adhere.

In a preferred embodiment, the coating is sheetlike, line shaped, stripe shaped, net shaped, point shaped and/or drop shaped. The Figures are referenced for this.

Preferably it is further provided that the primary dressing has a film having pores and/or perforations. Said film preferably consists of a thermoplastic film or of a polyolefin, for example PE. Such films are produced for example by the companies Tredegar or RKW.

The silicone coating may be applied to the film before introduction of the pores and/or perforations, or alternatively only after introduction of the pores and/or perforations.

Preferably it is further provided that the pores and/or perforations are structured in three-dimensional form.

Preferably it is further provided that the primary dressing has one rough and one smooth side. In this manner, a material is produced similarly to the product SORBION® Plus. This is described in patent application WO2007118652, to the entire content whereof reference is made here.

On application of the smooth side onto the wound, as well as the usual advantages of primary dressings (low adhesion to the wound, prevention of granulation of wound material into the wound dressing), a fluid-conducting function also comes into effect; thus rims are formed by the three-dimensional pores and/or perforations, which are positioned on the side facing away from the wound and prevent return flow of wound exudate into the wound.

On application of the rough side onto the wound, the primary dressing develops an abrasive action which is capable of breaking up biofilms and effecting a debridement. This action is described in patent application DE102012100842, to the entire content whereof reference is made here.

In a further preferred embodiment a coating is placed on the rough and/or on the smooth side—depending on which side is to be employed as wound contact side.

Preferably it is further provided that the primary dressing contains a gauze or a tissue containing pores and/or honeycomb lattice. Such products are for example known under the trade name Adaptic (consisting of a cellulose acetate network).

It is further provided that the primary dressing has a content of at least one heavy metal present in elemental or ionic form.

In finely divided form, heavy metals have a bactericidal action, which is attributable to the adequate formation of soluble heavy metal ions owing to the high reactive area.

By doping with at least one heavy metal present in elemental or ionic form, an antibacterial action can be imparted to the primary dressing, which decreases complications in case of wounds liable to infection (pressure ulcer, leg ulcer, burn wounds, etc.) and at the same time can increase the wear time of the wound dressing.

It is preferably provided that the at least one heavy metal present in elemental or ionic form is selected from the group comprising copper, zinc and/or silver.

The aforesaid bactericidal properties apply in particular for these three metals.

Preferably it is further provided that the heavy metals present in elemental or ionic form are applied onto the primary dressing by coating. Preferred coating methods are for example:

Chemical vapor deposition (CVD)
Flame coating (C-CVD)
Physical vapor deposition (PVD)
Plasma-enhanced chemical vapor deposition (PECVD)
Spin coating
Spraying
Dip coating
Vacuum evaporation
Sputtering The customary methods are known to those skilled in the art, and they are therefore able without further inventive activity to utilize the aforesaid methods for coating the primary dressing according to the invention with heavy metals present in elemental or ionic form.

Preferably it is further provided that the heavy metals present in elemental or ionic form are introduced into the primary dressing by coextrusion. In this the heavy metals present in elemental or ionic form can be introduced into the extrusion process, for example in the form of colloids, in the form of salts (preferably as chloride, sulfate or nitrate) or in the form of organometallic compounds.

Likewise, the coating or the material for the extrusion doping can consist of a combination of silver, zinc or copper and calcium phosphate (for example in the form of nanoparticles of calcium phosphate which are coated with silver, zinc or copper). The combination of one of the three heavy metals with calcium phosphate is for many germs up to 1000 times more lethal than conventional silver preparations. A decisive factor appears to be that bacteria use the carrier substance calcium for their metabolism. The 20 to 50 nanometer calcium phosphate particles are absorbed by the microorganisms as food and thereby disintegrated. As a result, thousands of 1 to 2 nanometer silver particles are released and exert their bacteriostatic action.

Preferably it is further provided that the primary dressing is a wound contact lattice.

It is further provided that the primary dressing additionally has punched holes, slits, incisions and/or recesses which serve to facilitate the passage of fluid.

These can for example be designed in the form of elongated holes, squares and/or crosses. This is particularly advantageous when the material consists of a three-dimensional film material with apertures or perforations turned towards the outside or towards the wound, which impart to the wound care product a rough outer surface and hence abrasive properties. Through the abrasive properties, the exudation of the wound is stimulated, and fluid accumulations can occur in the upper wound area, which have to be conducted away. Said punched holes, slits, incisions and/or recesses ensure facilitated passage and effective and rapid absorption of the exudate which is generated through use of the primary dressings according to the invention.

Further, a wound dressing is provided, having a covering which at least partially consists of a primary dressing according to one of the previous patent claims.

Such configurations, in which a primary dressing in strip form, having pores, perforations or honeycomb lattices forms a part of the covering of a wound dressing, are often used in wound care. Thus for example the products CUREA® P2 and VLIEWASORB™ have such a primary dressing—admittedly without the said heavy metals—as an integral component of their covering.

It is preferably provided that said wound dressing has a wound exudate-absorbing body. The wound exudate-absorbing body preferably contains at least one material which is selected from the group comprising a mat, in particular made from an airlaid of said yarns or fibers of super-absorbent polymers with incorporated superabsorbent polymers and/or a loose filling of superabsorbent polymers. Said airlaid mat can preferably have an essentially flat material section of absorbent material, which for example consists of an absorbent nonwoven of said fibers with superabsorbent polymers distributed therein.

This wound exudate-absorbing body can correspond to the absorbent insert which is contained in one wound dressing from the applicant of the present invention, as disclosed for example in WO03094813, WO2007051599 and WO0152780 marketed under the trade name "SORBION SACHET®". The disclosure content of said documents is to be appended in its entirety to the disclosure content of this document.

In another configuration, the wound exudate-absorbing body can also form a core which has, optionally flock-like, fibers or yarns of superabsorbent polymers in granule form, wherein the granules are glued or welded onto the fibers or yarns at several heights and the granules are distributed over more than 50% of the whole height of at least one section of the core, wherein blended regions of granules and fibers are present. The content by weight of the superabsorbent polymers here can preferably lie in the range between 10-25 wt. %. Similar designs are known from conventional incontinence materials and like sanitary napkins are known for their padding properties.

The microfibers already mentioned above are also possible for the absorbent body. These can be used both alone and also in combination with other fibers and the superabsorbent polymers.

In another form, the wound exudate-absorbing body can also contain at least one flat layer containing fibers or yarns of superabsorbent polymers, onto which superabsorbent polymers in granule firm are glued. Thereby in a preferred form, a structure of the body is obtained which has at least three layers, wherein two covering layers surround a layer containing superabsorbent polymers.

Here, no mixtures of fibers and superabsorbent polymers are present in the plane, but only fixed adjacent positionings of the two materials. Here the optionally provided several layers can in a preferred embodiment also be physically compacted together by rolling, pressing, calendaring or similar methods. In addition, the body can have repeating patterns or variegations, such as for example a square pattern, a punched hole pattern or the like.

In a particular embodiment, it is provided that the wound care product, in particular the wound exudate-absorbing body; contains superabsorbent polymers. With a wound dressing, these can be incorporated into the absorbent body and/or into the covering, or else be located within the covering as a loose component. The latter arrangement requires a covering matched to the size of the superabsorbent polymers, wherein the superabsorbent polymers do not sift out of the covering. As stated below, both superabsorbent particles or else fibers are possible, which are present either as loose bulk material or else are incorporated into the surrounding material. With a wound cleaning pad, the fixing of the superabsorbent polymers must also be adapted to the format of the pad or cloth.

Superabsorbent polymers (SAP) are plastics which are capable of absorbing a multiple of their own weight—up to 1000-fold—of liquids. Chemically, these are a copolymer of acrylic acid (propenoic acid, C3H4O2) and sodium acrylate (sodium salt of acrylic acid, NaC3H3O2), wherein the ratio of the two monomers to one another can vary. Additionally, a so-called core crosslinker (CXL) which binds the long-chain polymer molecules to one another in places by chemical bridges "crosslinks" them is added to the monomer solution. Because of these bridges, the polymer becomes water-insoluble. On penetration of water or aqueous salt solutions into the polymer particle, it swells up and tightens this network at the molecular level, so that the water can no longer escape unaided.

The use of SAP in wound dressings for the absorption of exudate is already known from WO0152780 and WO03094813 from the applicant of the present invention, the content whereof should be added in its entirety to disclosure content of the present application. The term "exudate" refers to a wound fluid derived from the blood plasma via the inflammatory processes of wound edema. Just as the blood is responsible for the transport of nutrients and other messenger substances and hence for the supply to various parts of the body, the exudate quite similarly serves for the supply of the wound bed and the healing processes taking place therein. In order to fulfill this multitude of functions, it contains a broad spectrum of components, which results in a specific gravity which lies slightly above that of water. It thereby differs from the transudate, which is derived from non-inflammatory processes and has a markedly lower specific gravity with a low cell and protein content. Apart from the provision of nutrients for the fibroblasts and epithelial cells, the exudate coordinates the various processes of wound healing chronologically and spatially through its high content of growth factors and cytokines. These are mainly formed by thrombocytes, keratinocytes, macrophages and fibroblasts. They influence the motility, migration and proliferation of the various cells involved in wound healing. Thus the migration of cells into the wound bed is promoted likewise to the supply to the newly formed granulation tissue by angiogenesis. The wound cleaning is also supported by the exudate. It contains various serine, cysteine and aspartate proteases and matrix metalloproteinases, the activity whereof is strictly regulated and which degrade both existing and also newly formed collagen in the wound.

Components of the physiological exudate are in particular salts, glucose, cytokines and growth factors, plasma proteins, proteases (in particular matrix metalloproteinases), granulocytes and macrophages.

If within a few weeks there is not a clear progression of the wound healing process corresponding to the various phases of wound healing, then this is referred to as a chronic wound. However, exudative phases lasting longer than three days are already regarded as a complication and referred to as a pathological exudation, which can contribute to chronification of the wound. The underlying causes are mostly complex and may well also be of a systemic nature. However, on the basis of the importance of the exudate for wound healing explained above, it is not surprising that complications of wound healing are reflected in a markedly altered composition and action of the exudate.

Due inter alia to a concentration shift of the individual components of the exudate, in chronic wounds the normally healing-promoting exudate loses its beneficial action. In particular the content of inflammatory cytokines and proteases is significantly elevated in pathological exudate. Conversely, the content of growth factors is diminished. A particularly serious difference is found as regards the activity of the aforesaid matrix metalloproteinases. Apart from the preparation of the wound bed, they are also involved in the later conversion of the granulation tissue to scar tissue. These enzymes are normally formed as an inactive proenzyme and their activation regulated by corresponding inhibitors (tissue inhibitors of metalloproteinases, TIMPs), which at the same time themselves have a beneficial action on cell growth. In chronic exudate, the activity of the proteases appears elevated owing to disorders in this regulatory system, which possibly contributes to regression of the wound healing. As regards the content of its components, the pathological exudate has departed from the equilibrium conducive to wound progression. Various complications result from this, which contribute to the further deteriorating and chronification of the wound.

In connection with the wound care product according to the invention having at least one surface with abrasive properties, which is capable of breaking up biofilms located in the wound, and/or stimulating wound exudation, said components containing SAP are of particular importance.

Thus the specified of SAP serves to absorb the fragments and residues of the biofilm that are generated. Through the destruction of the biofilm, endotoxins and bacterial pathogenicity factors (in particular hemolysin and leukocidin) which can cause inflammation, allergies, shock (in particular anaphylactic shock and/or toxic shock syndrome) and fever (Herxheimer reaction) are sometimes also released. Said endotoxins and pathogenicity factors are absorbed by the content of SAP, so that said sequelae can be avoided.

In DE102007054127 from the applicant of the present invention, the disclosure content whereof should be added to that of the present application, these relationships are described in detail; in particular it is shown that SAP are capable of binding bacteria and bacterial endotoxins.

It is also particularly preferably provided that the wound exudate-absorbing body has a pattern of incisions and/or punched holes. These are preferably formed and/or arranged such that they facilitate the entry of fluid into the wound care product.

This feature presents special advantages in combination with a covering which imparts to the wound care product a rough outer surface and hence abrasive properties, for example of a three-dimensional film material with openings or perforations turned towards the outside or towards the wound, so as to ensure effective and rapid absorption of the exudate which is created by use of the wound care products according to the invention.

Also provided is the use of a primary dressing or a wound dressing as claimed in one of the previous patent claims in a negative pressure wound care system.

Such systems are for example disclosed in the documents DE202004017052, WO2006048246 and DE202004018245 from the applicant of the present invention, the disclosure content whereof should be regarded as belonging to the present invention.

From the first-mentioned, a device for wound treatment using negative pressure is known, having a gas-tight wound covering element which in the state applied on the patient's body forms a permanent space between the wound in question and the wound covering element, and at least one connecting point which is in contact with the space and via which the air present in the space can be evacuated, wherein the wound covering element is underlaid by at least one planar wound dressing absorbing the wound exudate, the volume whereof increases in the course of the absorption process, so that the absorbed wound exudates remain within the wound dressing and thus under the wound covering element until the removal of the wound dressing from the patient's body, the wound dressing is at least one layer of a textile segment enriched with superabsorbents, which is surrounded with a fluid-permeable covering, and the layer viewed from above its flat side has an area which is 3% to 90% smaller than that of the covering, so that the wound dressing when close to its total filling capacity can approximate to a circular shape in cross-section.

From the second, a multicomponent dressing for wound treatment of the human or animal body with use of negative pressure is known, which contains: a wound covering element for application onto skin and mucosa surface, at least one connecting point which is in contact with the wound space and via which the substances present in the wound space can be evacuated, wherein this contains superabsorbent polymers, wherein the absorbed wound exudates remain bound to polymers in the wound space until removal from the wound space, wherein the polymers through their binding capacity promote reciprocal synergies with the subatmospheric pressures.

From the last-mentioned, a drainage device for wound treatment with use of negative pressure is known, which contains a gas-tight wound covering element consisting of film-like material, which in the state where it is laid on the patient's body is adhesively fixed on the skin surface around the wound area and forms a sealed space between the wound in question and the wound covering element, at least one drainage tube which is insertable into the space, via which the substances present in the space can be evacuated, and at least one wound dressing absorbing the wound exudates, arranged within the space, which has at least one layer of a textile segment enriched with superabsorbents, which is surrounded with a fluid-permeable covering, whereby the absorbed wound exudates remain within the wound dressing and thus under the wound covering element until the removal of the wound dressing from the patient's body, and whereby the wound covering element has a gas-tight sealable handling aperture through which the wound dressing is insertable into the space, and removable from the space.

DESCRIPTION OF THE DRAWINGS

The invention is non-restrictively illustrated by way of example in the attached drawings, where.

DETAILED DESCRIPTION OF PREFERRED EMBODIMENTS

Figure 1:
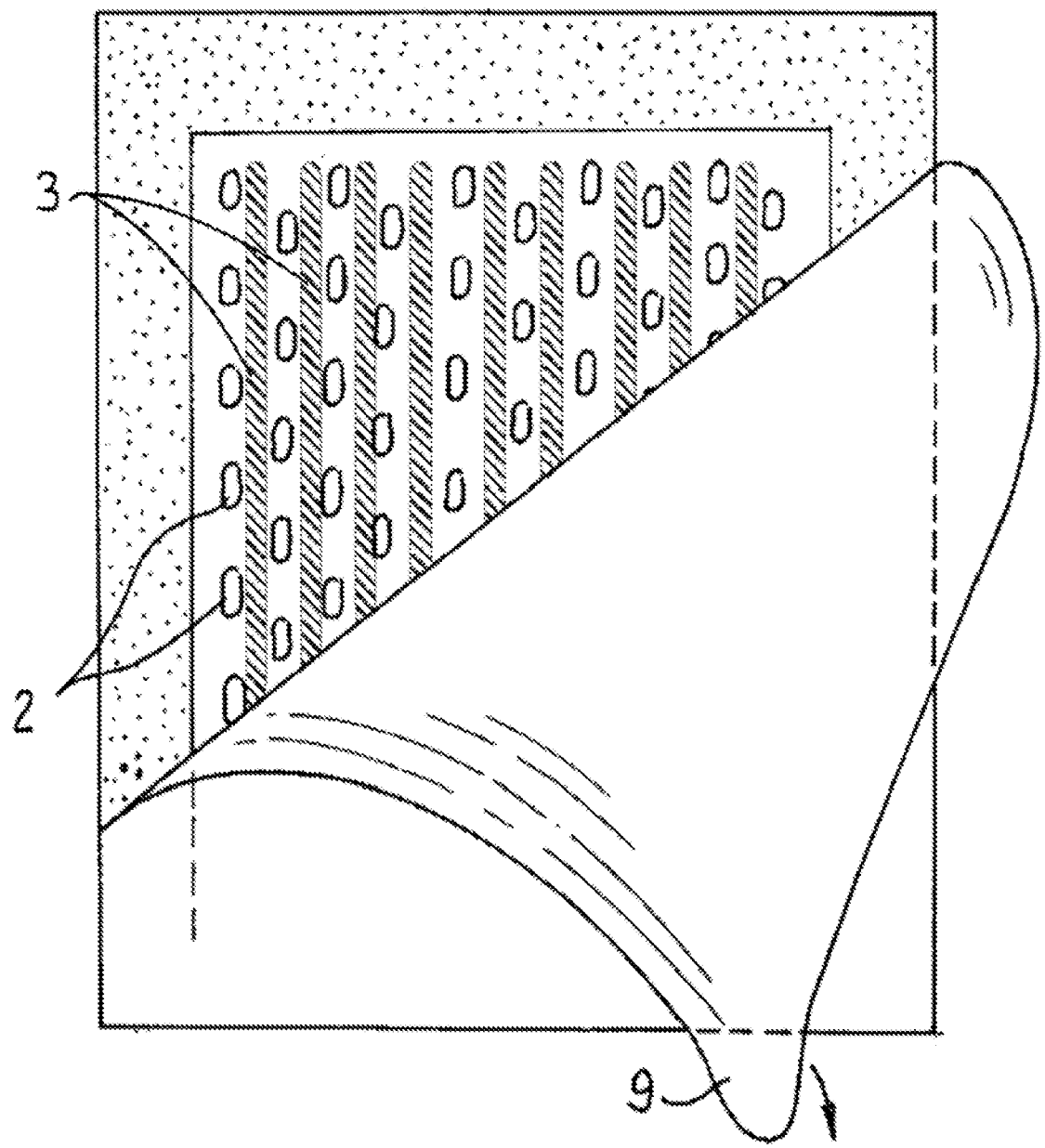
FIG. 1 shows a top plan view of a fluid-permeable primary dressing in strip form with perforations.

FIG. 1 shows a fluid-permeable primary dressing in strip form, having perforations 2 which enable the passage of fluid. The primary dressing is accommodated in a sterile pack 9. The primary dressing has a sheetlike coating of silicone. FIG. 1 further shows a silicone coating in the form of silicone bands 3 applied to the primary dressing in stripe-shaped form.

Figure 2:
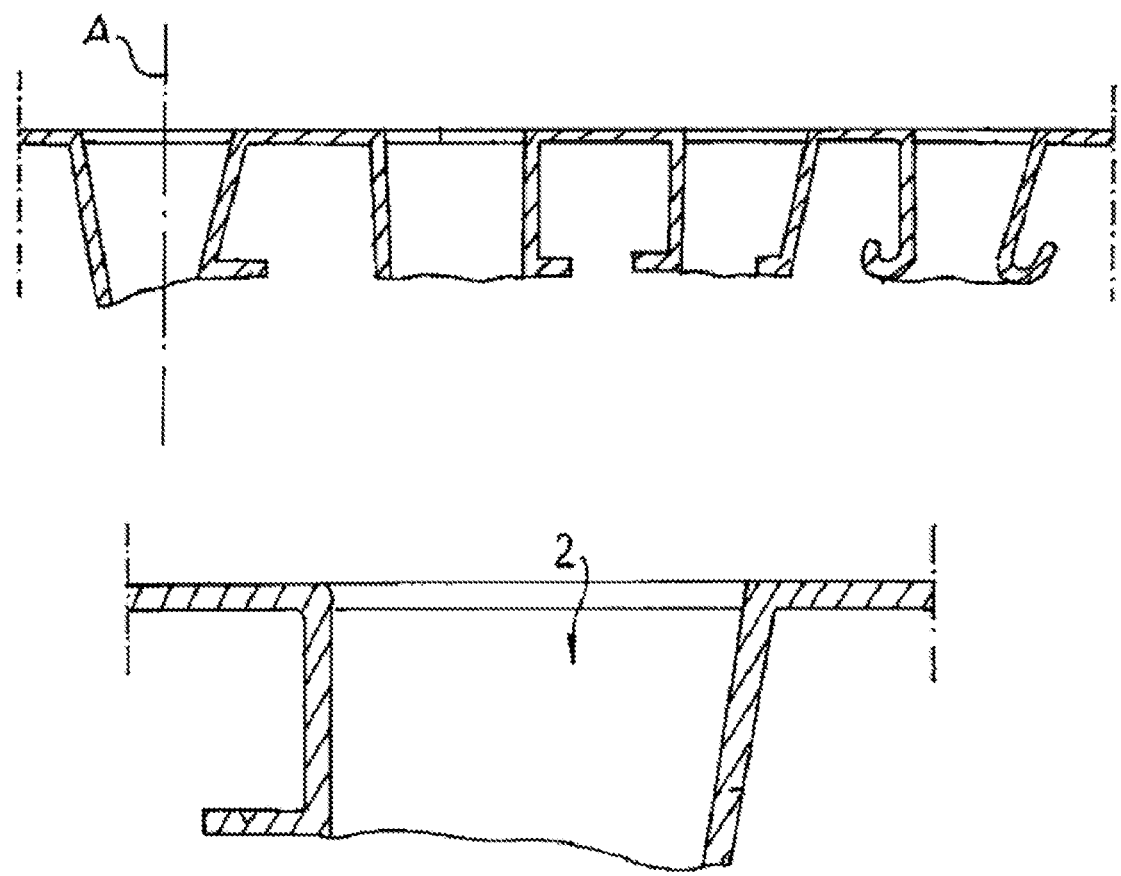
FIG. 2 shows a cross-section views of perforations with projections.

FIG. 2 shows said perforations in cross-section. Here it can be discerned that the latter preferably have conically shaped walls, which in turn extend irregularly into projections oriented approximately perpendicular to a perforation axis A. These projections can also be bent over inwards or outwards, as shown on the right-hand side of FIG. 2.

The structure of the perforations described contributes to the fact that the absorbed wound exudate can only flow back in the direction of the wound with difficulty, hence said projections are not absolutely necessary.

Figure 3:
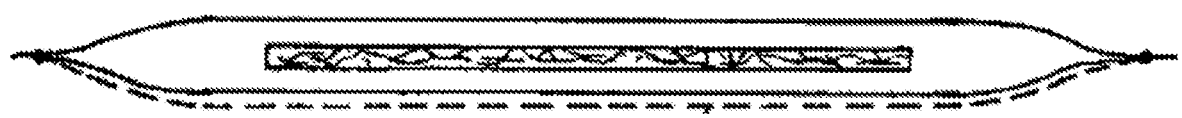
FIG. 3 shows a cross-section-view of a wound dressing with a planar absorption body and a covering.

FIG. 3 shows a wound dressing with a planar absorption body and a covering which in sections consists of a primary dressing as claimed in one of the previous patent claims (dashed line). Said primary dressing can augment (double) the actual covering wall on the side in question or else replace it (not shown). Said wound dressing additionally has a wound exudate-absorbing body.

Deviating from the portrayal in FIG. 3, the primary dressing can also surround the absorption body on all sides, and thereby augment or else replace the covering. The welds (for example ultrasound welds), differently from the representation can also be bent inwards (the covering thus being as it were "drawn leftwards"), in order to form soft edges pleasant for the wound contact.

Figure 4:
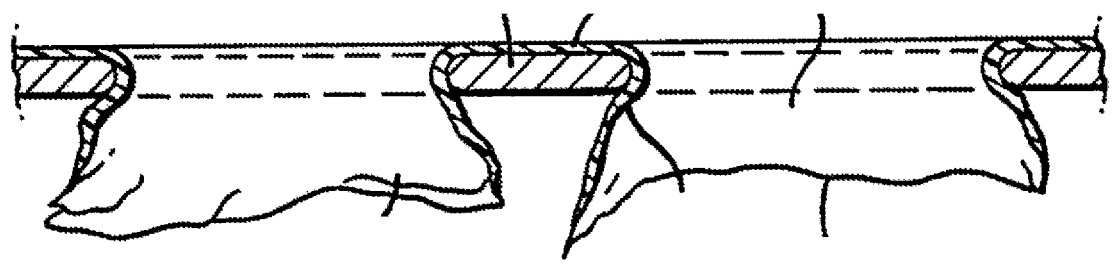
FIG. 4 shows a cross-section view of perforations without projections.
Figure 4:
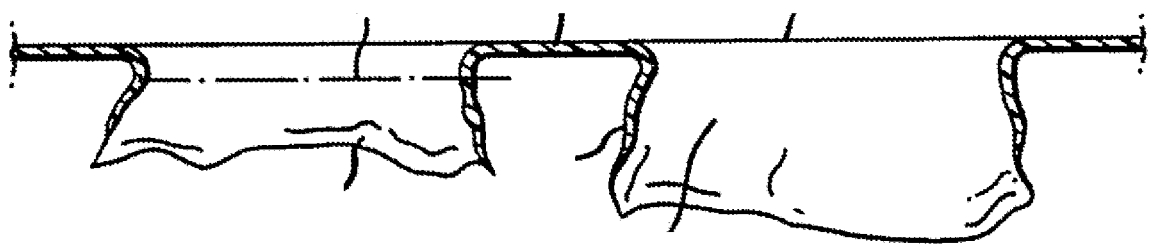

FIG. 4 also shows said perforations in cross-section, this time in a naturalistic representation. Here it can be seen that the projections described in FIG. 2 no longer occur.

Figure 5:
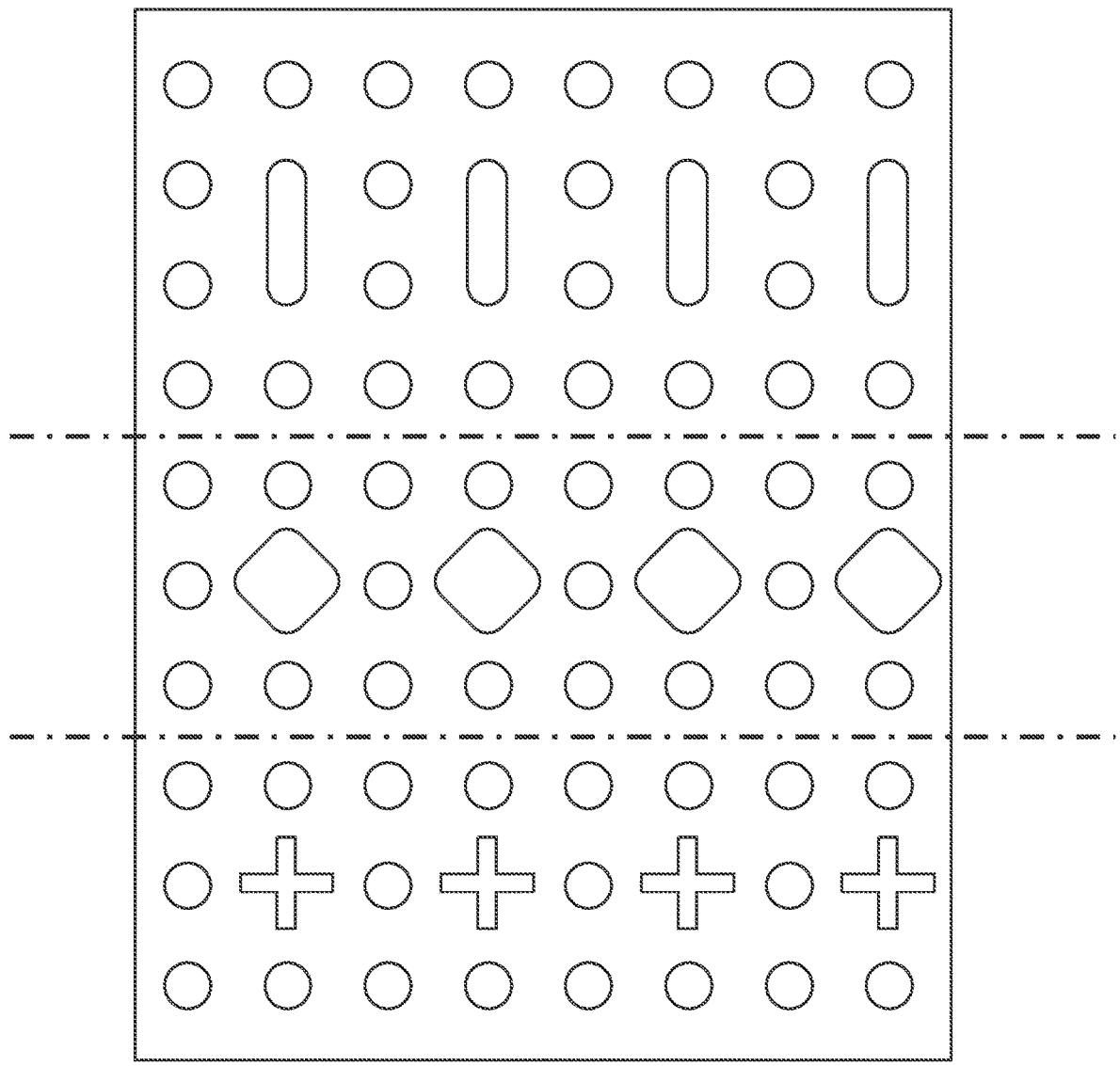
FIG. 5 shows a top plan view of another embodiment of a fluid-permeable primary dressing in strip form with perforations.

FIG. 5 shows a fluid-permeable primary dressing in strip form similar to that in FIG. 1, having perforations. Here also, the perforations open towards the wound and thus form said rough, abrasively acting surface. The fluid-permeable primary dressing in strip form can partly or wholly act as the covering for a wound care product containing an absorbent body. Further, this wound care product has punched holes, slits, incisions and/or recesses for example in the form of elongated holes, squares and/or crosses, which serve to facilitate the passage of fluid.

This is particularly advantageous when the material consists of a three-dimensional film material with openings or perforations turned outwards or towards the wound, which impart to the wound care product a rough outer surface and thus abrasive properties. Through the abrasive properties, the exudation of the wound is stimulated and fluid accumulations in the upper wound area can occur, which have to be removed. The said punched holes, slits, incisions and/or recesses ensure facilitated passage and effective and rapid absorption of the exudate which is created by use of the wound care product according to the invention.

Figure 6:
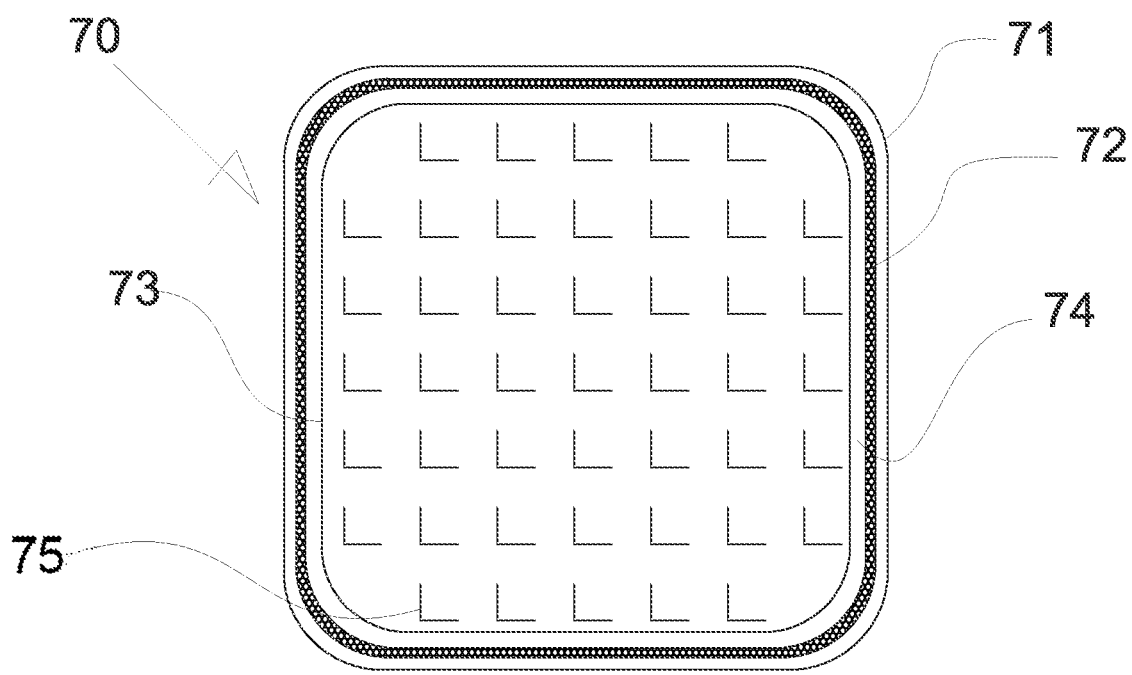
FIG. 6 shows a top plan view of yet another embodiment of a wound care product.

FIG. 6 shows a top view of a wound care product 70 having a covering 71 with a weld 72, which consists of a primary dressing according to the invention, preferably with openings or perforations turned outwards, which impart to the wound care product a rough surface and hence abrasive properties, and a flat absorption body 73 of a nonwoven or airlaid material containing superabsorbent polymers.

The covering forms an expansion space 74 so that it is ensured that the absorption body can increase in volume on absorption of fluid and is not restricted by the covering. The planar absorption body 73 has a pattern of L-shaped incisions 75 which are introduced into the absorption body by means of an appropriately shaped punch tool. In this way, the entry of fluid into the wound care product is considerably facilitated. This feature displays particular advantages in combination with the covering of three-dimensional film material with openings or perforations oriented outwards, which impart to the wound care product a rough outer surface and hence abrasive properties.

Differently from the representation in FIG. 6, the weld 72 (for example ultrasound weld) can also be turned inwards (the covering thus being as it were "drawn leftwards"), in order to form soft edges pleasant for the wound contact.

Figure 7:
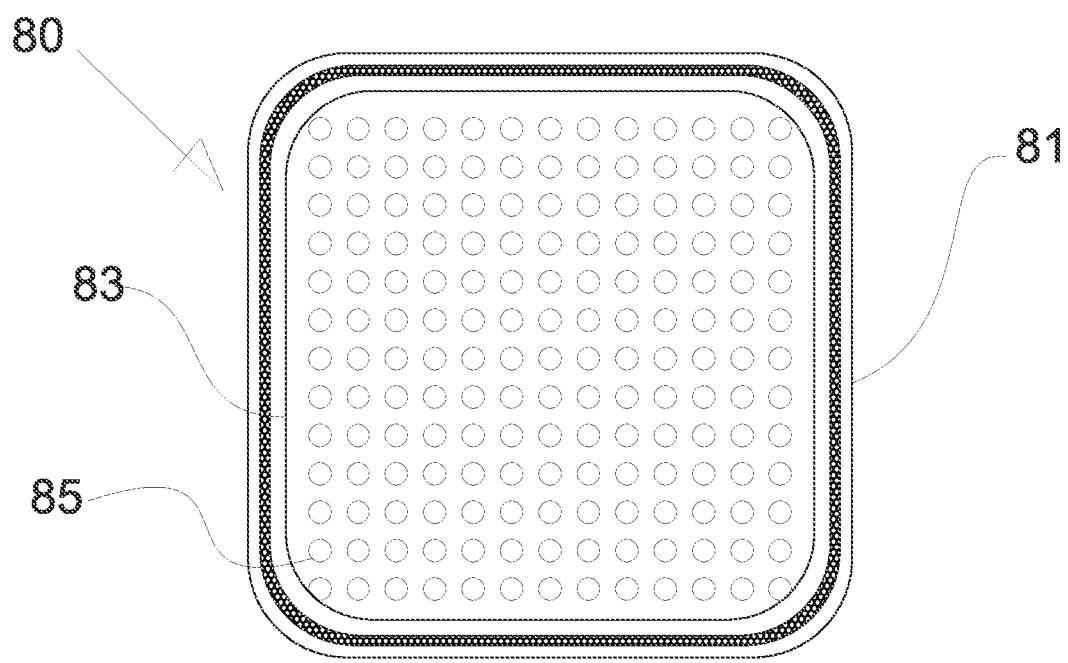
FIG. 7 shows a top plan view of yet embodiment of a wound care product.

FIG. 7 shows a top view of a wound care product 80, having a covering 81 formed similarly to that in FIG. 1 from the primary dressing according to the invention and a planar absorption body 83 of a nonwoven or airlaid material containing superabsorbent polymers. The planar absorption body 83 has a planar pattern of punched holes 85, which are introduced into the absorption body by means of an appropriately shaped punch tool. In this way, the entry of fluid into the wound care product is considerably facilitated. Further, the adaptability of the originally relatively stiff absorption body is increased, so that a wound care product is produced which adapts gently to the wound relief, is experienced by the patient as very soft and pleasant and through the close contact with the wound can fully exercise its wound exudate-absorbing function.

Figure 8:
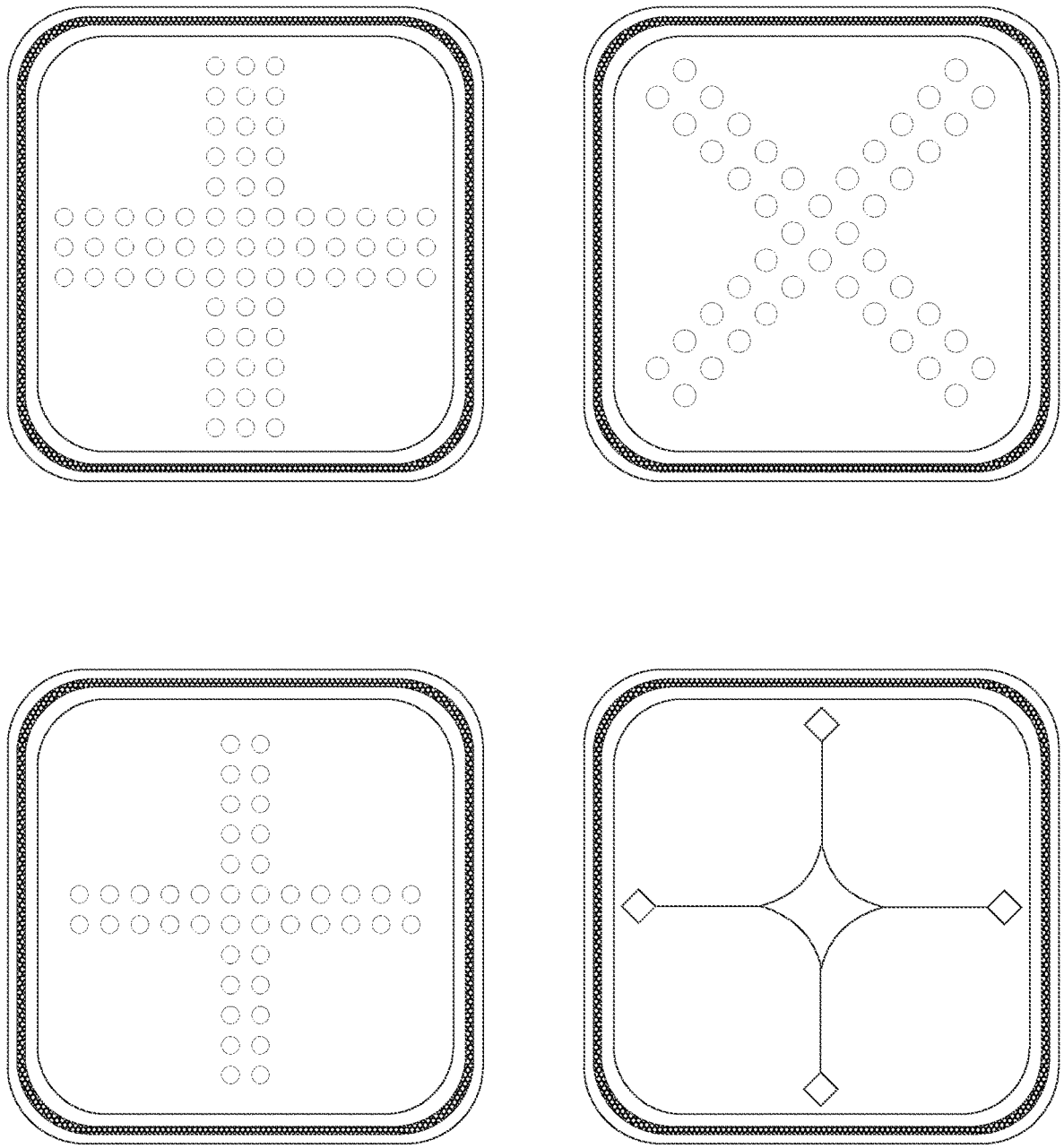
FIG. 8 shows top plan views of further embodiments of wound care articles.

FIG. 8 shows further embodiments of the wound care product according to the invention, wherein the punched holes and/or incisions, which are sometimes implemented together in one wound care product, facilitate entry of the wound fluid into the wound care product.

Figure 9:
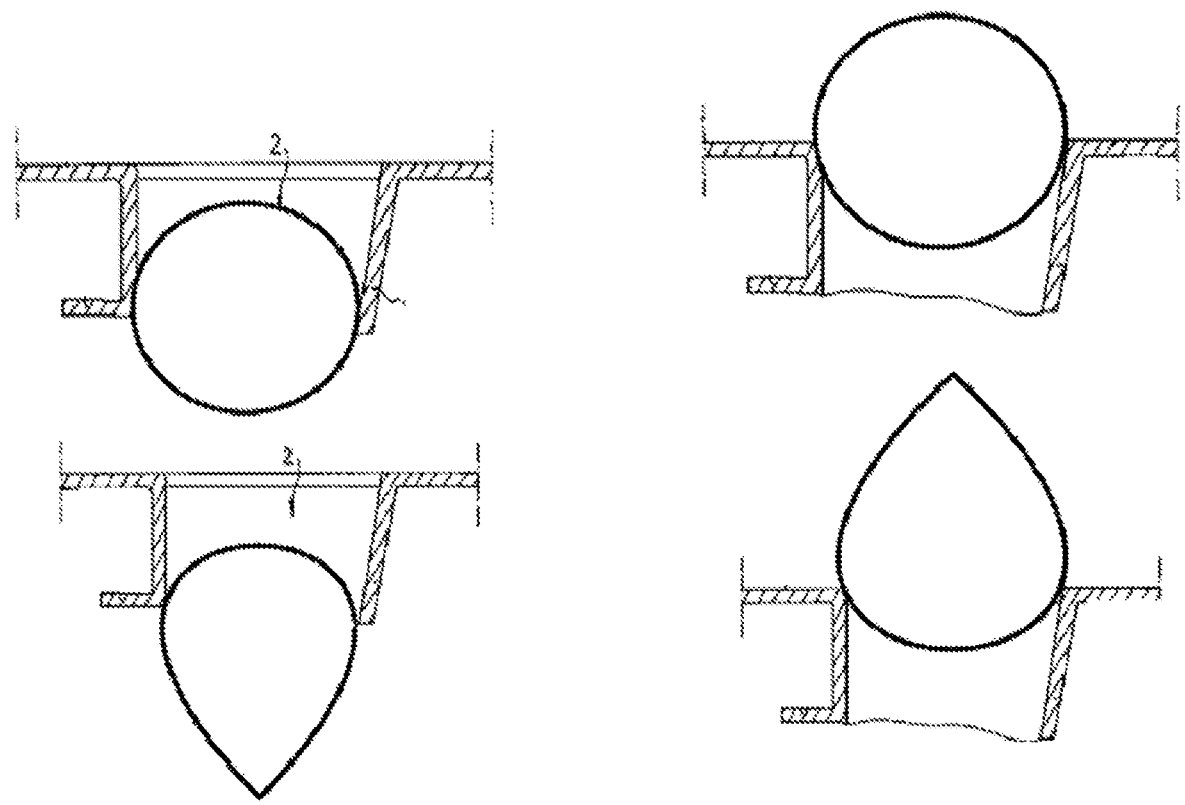
FIG. 9 shows a cross-section view of perforations.

FIG. 9 shows the perforations once more in cross section. Silicone coatings are depicted on said perforations by way of example after application thereto in cross-sectionally point-, drop- or line-shaped form.

What is claimed is:

1. A fluid-permeable primary dressing in strip form, said primary dressing comprising:
   a film provided with a plurality of pores or perforations arranged in linear rows; and
   discrete stripe-shaped bands of a silicone coating applied to the film that separate the linear rows from each other;
   wherein said pores or perforations enable the passage of fluid,
   wherein said linear rows are parallel to each other,
   wherein the pores or perforations are in three-dimensional form, and
   wherein the primary dressing is a wound contact lattice.

2. The primary dressing as claimed in claim 1, wherein the primary dressing has one rough and one smooth side.

3. The primary dressing as claimed in claim 2, wherein the coating is placed on the rough and/or the smooth side.

4. The primary dressing as claimed in claim 1, wherein the primary dressing further comprises a gauze or a tissue containing pores and/or honeycomb lattice.

5. The primary dressing as claimed in claim 1, wherein the primary dressing additionally has punched holes, slits, incisions and/or recesses which serve to facilitate the passage of fluid.

6. A wound dressing having a covering which at least partially consists of a primary dressing as claimed in claim 1.

7. The wound dressing as claimed in claim 6, wherein said wound dressing contains a wound exudate-absorbing body.

8. The wound dressing as claimed in claim 7, wherein the wound exudate-absorbing body has a pattern of incisions and/or punched holes.

9. The wound dressing as claimed in claim 8, wherein the pattern of incisions and/or punched holes are formed and/or arranged such that they facilitate the entry of fluid into the wound dressing.

10. The wound dressing as claimed in claim 7, wherein the wound exudate-absorbing body is a mat with incorporated superabsorbent polymers and/or a loose filling of superabsorbent polymers.

* * * * *